United States Patent [19]
Olichney et al.

[11] Patent Number: 5,421,829
[45] Date of Patent: Jun. 6, 1995

[54] ULTRASONIC SURGICAL HANDPIECE AND AN ENERGY INITIATOR

[75] Inventors: Michael D. Olichney; Michael S. Klicek, both of Boulder, Colo.; Emery S. Rose, New York, N.Y.; Alan Broadwin, Brooklyn, N.Y.; Alexander S. Kreizman, Beechhurst, N.Y.

[73] Assignee: Valleylab Inc., Boulder, Colo.

[21] Appl. No.: 242,516

[22] Filed: May 13, 1994

Related U.S. Application Data

[63] Continuation of Ser. No. 982,936, Nov. 30, 1992, abandoned.

[51] Int. Cl.⁶ .............................................. A61B 17/32
[52] U.S. Cl. ...................................... 606/170; 604/22
[58] Field of Search .................... 604/22; 606/167–171

[56] References Cited

U.S. PATENT DOCUMENTS

| | | |
|---|---|---|
| 4,223,676 | 9/1980 | Wuchinich et al. |
| 4,493,694 | 1/1985 | Wuchinich ............................ 604/22 |
| 4,504,264 | 3/1985 | Kelman ................................ 604/22 |
| 4,587,958 | 5/1986 | Noguchi et al. |
| 4,747,820 | 5/1988 | Hornlein et al. |
| 4,886,060 | 12/1989 | Wiksell ................................ 604/22 |
| 4,898,574 | 2/1990 | Uchiyama et al. ................... 604/22 |
| 5,139,509 | 8/1992 | Fischer et al. ....................... 604/22 |
| 5,162,044 | 11/1992 | Gahn et al. .......................... 604/22 |

*Primary Examiner*—Jerome L. Kruter
*Attorney, Agent, or Firm*—Peter C. Richardson; Lawrence C. Akers; Aaron Passman

[57] ABSTRACT

An ultrasonic oscillator drives a tool at a set frequency. An amplitude control runs the oscillator to set the vibration level. A frequency regulator joins the amplitude and the oscillator. A control feedback loop, in the frequency regulator, keeps handpiece linear dynamics. An operational transconductance amplifier, in the oscillator, governs gain of the loop. A circuit connects to the control to retard the rate of current application over time to the amplifier. The circuit has switching to either retard the rate or reset for start up. The amplifier is a current output device with current directly proportional to the bias current and input voltage with bias as gain change for the loop. The circuit limits the bias to the amplifier to modify frequency response and output current. A capacitor delays application of the bias to the amplifier. Replaceable tools of various lengths or shapes positioned along an axis vibrate for surgery at the frequency and a wave length. Tools longer than one wavelength and of configurations tuned to oscillate around the frequency resonate as a function of their material, length and configuration. A flue surrounds the tool and has a hollow elongate semi rigid central body about an axis with a funnel, at one end thereof and a nozzle, at the other to direct annular irrigant/coolant flow therethrough. The funnel and nozzle are resilient. Reinforcing ridges, inside the nozzle, act to maintain concentricity between the flue and nozzle tip and channel irrigant thereabout.

13 Claims, 5 Drawing Sheets

ULTRASONIC SURGICAL HANDPIECE AND AN ENERGY INITIATOR

This is a continuation of Ser. No. 07/982,936, filed Nov. 30, 1992, now abandoned, entitled, ULTRASONIC SURGICAL HANDPIECE AND AN ENERGY INITIATOR.

FIELD OF THE INVENTION

This invention relates to an ultrasonic surgical handpiece and an energy initiator to maintain the vibration and linear dynamics during start up and under loads. In addition, a flue construction and an elongate tapered pipe tool structures as part of the ultrasonic surgical handpiece are driven by a vibrating driver powered by a circuit including the energy initiator.

BACKGROUND OF THE DISCLOSURE

Described herein are an ultrasonic surgical handpiece with the energy initiator circuit to begin and maintain the vibrations and linear dynamics of the elongate tapered pipe tool. The flue is coaxially about the tool.

U.S. Pat. No. 4,223,676 discloses an ultrasonic surgical handpiece having a longitudinally vibrating cutting tool ending in a tip with a flue to surround the vibrating tool. The disclosure of '676 is incorporated herein by reference and made a part of this disclosure since the surgical instrument therein is substantially refined and improved by that disclosed and claimed herein. Handpieces made in accordance with the teachings of the '676 patent have tools that were less than four inches long and even with extenders less than seven inches long. Heretofore the need for a tool that was greater than seven inches was unsatisfied and the flue and oscillating electronics needed to serve with such an elongate tool were undeveloped.

U.S. Pat. No. 4,747,820 owned by the assignee in this present disclosure has a rigid plastic flue constructed so that the body thereof may be rotated relative to a flue adapter, i.e., the piece that attaches to the distal end of the handpiece. The body and adapter are two separately made rigid plastic parts for allowing the relative rotary motion therebetween so that alignment may be achieved particularly where there is a curve in the flue body to accommodate a curved tool. An alternate flue of flexible polymer with supporting ribs is shown and described as received on a rigid adapter with an appropriate conjugating configuration.

While it might seem logical that an elongate tool requires a longer flue to supply irrigation and cooling fluid to the preaspiration holes near the tip of the elongate tool, many unsolved technicalities need resolutions which go beyond the mere extension of the length of the components. With increase in length the structure of the flue needs improvement to have the requisite strength and to provide the needed cooling flow to cover all of the increased size of the elongate tool. The flue disclosed herein is preferably of a soft polymer so that it will not injure the patient and in order to seal to the hand piece in a gasket like easily used way. Soft polymers such as silicon rubber have very little beam or bending strength and consequently, sag without support from the elongate tool or even with the elongate tool disposed coaxially therewithin the flue could lean under the force of gravity so as to be against the elongate tool, thus damping the tool vibrations. Circumferential or surround coolant is thus hampered by any off center disposition of the flue and the need to maintain concentricity between the flue and the elongate tool remains an unresolved problem.

In addition the dispersion of the irrigation fluid so as to equally access all side and areas of the elongate tool is a problem relative to length. The fluid flow tends to be influenced by gravity as well as the flue deflection. That is, the distance from the support or supply to the distal end increases the problem. Uniform circumferential distribution is difficult with a long flue.

To initiate the vibration in an elongate tip the electronic oscillating circuitry requires particular attention to avoid start up transient overshoots causing the electromechanical oscillating system to equilibrate (or lock up) on an unwanted adjacent resonance. Said adjacent unwanted resonances are present, in particular, due to a long mechanical vibrator in that it has a lower fundamental resonance. The harmonics are integral multiples of the fundamental resulting in a closer spacing, in the frequency domain (of harmonics, or poles), as a function of vibrator length. For example, U.S. Pat. No. 4,587,958 has a starting impulse reducing circuit to prevent transient current from over driving the power amplifier by maintaining the waveform at a predetermined flat amount instead of an initiating spike or overshoot resulting during start up transient conditions. While it is recognized that peak current waveform suppression is useful to prevent spikes that can be two or more times greater that required, a circuit to control the rate of power application to an operational transconductance amplifier is not disclosed. It is now appreciated that the peak initiating current is not the only factor affecting amplifier performance. For consistent operating characteristics after starting and under loads the rate at which power is supplied to the amplifier in an oscillating circuit must be specifically controlled in a manner not disclosed in '958. Normal variations in the response characteristics of amplifiers can greatly influence the manner in which any specific amplifier of a particular type will respond to input power. Reduction of such variations and the uniform responses are desired.

A difficulty with merely applying power to the electronic circuitry that drives a mechanical reverberating system results from the tuning of the resonance frequency of the mechanical structure designed to vibrate in harmony with the spring constant of the system. An electrical driving circuit is inherently flexible and can oscillate at several frequencies more readily than any mechanical system. Consequently, the driving impetus of the electronic circuit can excite the mechanical structure at different frequencies than the intended resonance frequency. There are many mechanical resonant modes of acoustic vibrators that are independant of drive afforded by the electronics. When that occurs, the mechanical system will vibrate in a manner that does not produce useful displacement and the energy output from the electrical oscillator is wasted. Filtering can be used to assure that the driving frequency is identical with the harmonic of the mechanical system but that requires a complicated circuit design and can not be retrofitted to an existing oscillating circuit. A way to control the initiation and maintenance of the oscillation so that the operating frequency is at the preferred resonant frequency of the mechanical system is required.

SUMMARY OF THE INVENTION

The energy initiator includes an electronic oscillator for driving an ultrasonic surgical handpiece preferably operating at a predetermined frequency of about 23 kilohertz. An amplitude control may operate the electronic oscillator permitting the setting of the level of ultrasonic vibration. It is preferred that a frequency regulator be connected between the amplitude control and the electronic oscillator. A frequency control feedback loop may be part of the frequency regulator to maintain the linear dynamics of the ultrasonic surgical handpiece about the predetermined preferred frequency.

An operational transconductance amplifier may be included as part of the electronic oscillator for controlling gain of the frequency control feedback loop. A circuit is preferably connected to the amplitude control for retarding the rate of current application per unit of time to the operational transconductance amplifier thereby ameliorating the effects of transients on the ultrasonic instrument during start up and otherwise. The circuit may include switching systems to in one direction retard the rate of current application and in the other direction of current flow reset the circuit. The operational transconductance amplifier is preferably a current output device with its output current directly proportional to the bias current and input voltage thereto. During operation the bias current may act as the gain or amplitude adjustment for the frequency control feedback loop. The circuit provides a soft start that may also limit the bias current applied to the operational transconductance amplifier thereby modifying the frequency response and output current therefrom during start up and/or limiting the peak bias current applied thereto. The soft starting circuit may include a resistance/capacitance network for setting the delay of the application of the full bias current to the operational transconductance amplifier.

The ultrasonic surgical handpiece may include replaceable ultrasonic tools of various lengths or configurations. A housing gripped proximally controls the handpiece during use. A transducer may be within the housing and positioned along an axis thereof. The transducer is selected or designed to have its primary resonance for oscillating around the preferred frequency and at a length along the axis with motion sufficient for surgery. A connecting member is fitted to the transducer and preferably extends distally from the transducer along the axis but within the housing. Pipe tools are replaceably attachable to the connecting member so that each pipe tool may be of a different length and/or configuration tuned so that the assembly of tool, connecting member and transducer oscillate around the preferred frequency and/or wave length. Wave length equals the speed of sound in material divided by frequency of operation. The soft starting or energy initiator circuit may be used in connection with an electronic oscillator for vibrating the replaceable tools. The length of the replaceable attachable tools may be a function of the material that the pipe tool is made, and its configuration whereby they are tuned to resonate at the preferred predetermined frequency, i.e., 23 kilohertz. The pipe tools are most preferably longer than one wave length or at least five-quarter wave lengths or seven-quarter wave lengths.

A flue for directing coolant to the pipe tool of the ultrasonic surgical handpiece may include a central body that is hollow, elongate and semi-rigid for extending concentrically about and coaxially to an axis passing centrally therethrough and through the pipe tool. A funnel is most preferably at one end of the central body and is proximally positioned to first receive the pipe tool vibrating tip when inserted therewithin and therethrough. A nozzle is opposite the funnel and attached to the central body. The nozzle tapers toward the distal vibrating tip of the ultrasonic surgical handpiece for directing annular flow of fluid from an annular space between the pipe tool and the central body. The funnel and nozzle are preferably made of a resilient material having a durometer which is softer than that of the central body. The central body is preferably of a higher durometer. The modulus of elasticity of the central body is most preferably greater than the modulus of the elasticity of either the funnel or the nozzle. The central body may be made of a separate piece that is preferably extruded transparent polymer such as polysulfone tubing. The nozzle and funnel may be made of molded silicone rubber and connected to one another by a recess or reduced diameter therebetween such that the recess may be surrounded by the extruded transparent tube for support.

The central body may separately, preferably and alternately be made of a molded construction of silicone rubber having a durometer higher than the funnel which may be bonded to the proximal portion of the central body. The nozzle may be more flexible than the central body although molded of the same silicone rubber because of its lesser cross sectional area.

The funnel may, on either flue construction, include a shouldered opening for receiving a tube for supplying cooling and preaspiration fluid. Reinforcing ridges may, on either connection, extend longitudinally inside the nozzle to act as a concentric support to coaxially position the nozzle relative to the vibrating tip whereby fluid passing in the annular space may preferably be channelled between the ridges.

DETAILED DESCRIPTION OF THE INVENTION

The claims are not limited to the structure for an ultrasonic surgical handpiece, a flue or an energy initiator to maintain the vibration and linear dynamics described and illustrated by way of example and specifically explained. The claims are to be considered in view of the existing knowledge of skilled artisans in the Field prior to the inventions defined by the language oft he claims herein, as amended or considered in view of knowledge of skilled artisans prior to these inventions. As used throughout this disclosure proximal or posterior has the meaning near the user and distal or anterior is near the patient. The reference numbers as seen in the several figures are identical wherein the components are the same.

Figure 1:
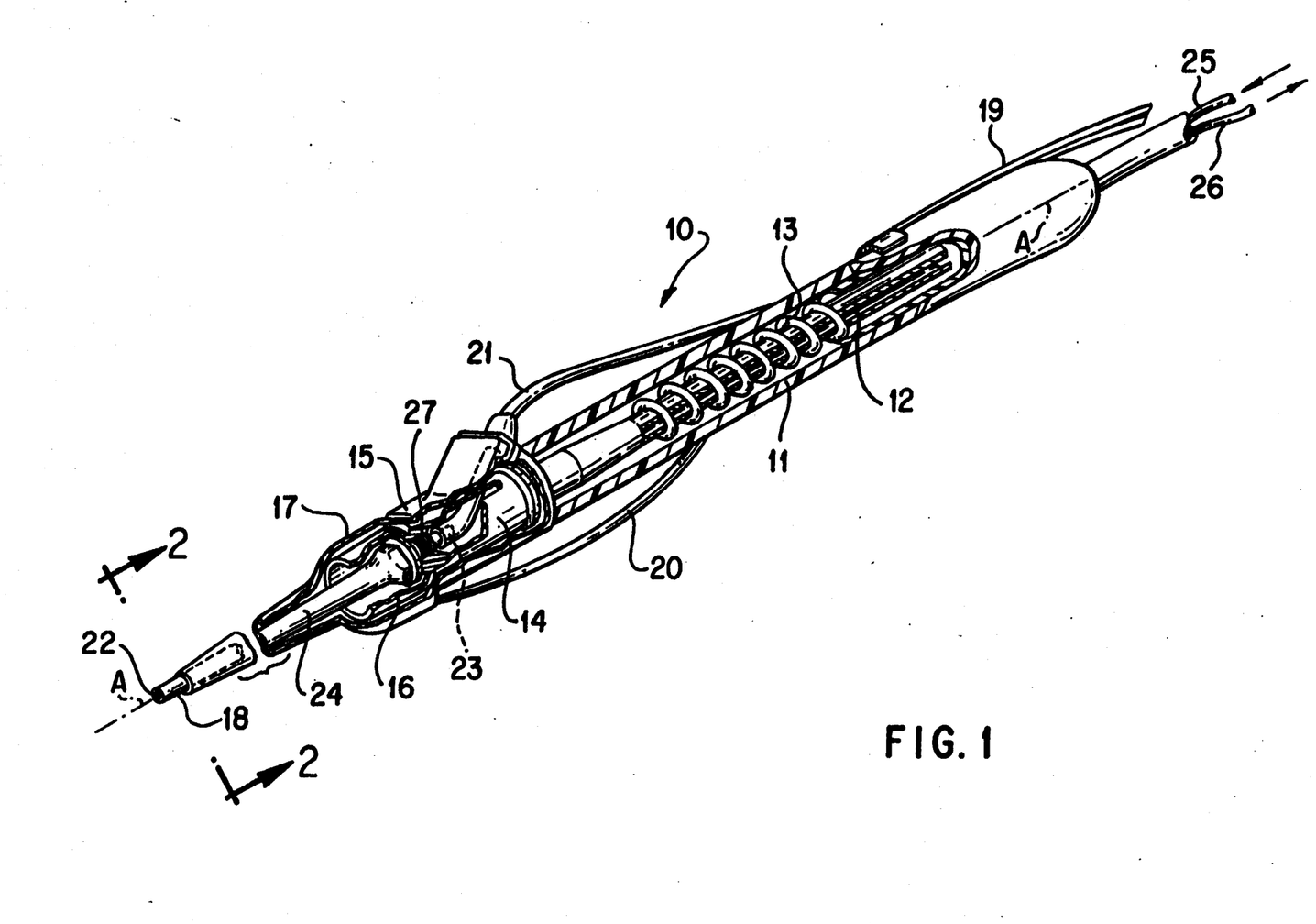
FIG. 1 is a perspective view of an ultrasonic surgical handpiece with part of the housing thereof removed so as to show the inside and the components therein.

FIG. 1 is a perspective view partially in section showing an ultrasonic surgical handpiece 10, including a housing 11 that encloses a transducer 12, an electric coil 13 and a connecting member 14 extending axial therethrough along an axis A which represents the longitude for the ultrasonic surgical handpiece 10. In front of the housing 11 there is a nose cone 15 tapered from the housing 11 to a distal end 16 thereof to which mounts a nose cone extending flue 17 thereabout to coaxially surround an axially vibrating metal fragmenting or cutting pipe tool 24. The axially vibrating cutting pipe tool 24 is preferrably metal, but might be otherwise, and tip 18 of pipe tool 24 extends longitudinally along axis A beyond the flue 17. A CUSA System 200 made by Valleylab, 5920 Longbow Drive, Boulder, Colo., has been used to drive the altered components disclosed herein.

A manifold assembly 19 composed of two tubes 20 and 21 for irrigation and suction, respectively lies atop and along the housing 11 to reside parallel to axis A. Tube 20 connects to the flue 17 near distal end 16 so as to feed sterile irrigation and cooling fluid down through the flue 17 for flow toward the tip 18. The vibration introduced into the tip 18 by means of the connecting member 14 generates an acoustic wave or stress resulting in the transformation of some energy into heat. The suction tube 21 draws fluid through at least one preaspiration hole 18a (small of size and shown only in FIGS. 2, 4 and 5, as will be described hereinafter that provides a portal between the flue 17 and a bore 22, see FIG. 3). The bore 22 of the pipe tool 24 extends between the tip 18 and a connection 23 for tube 21.

Figures 2, 3:
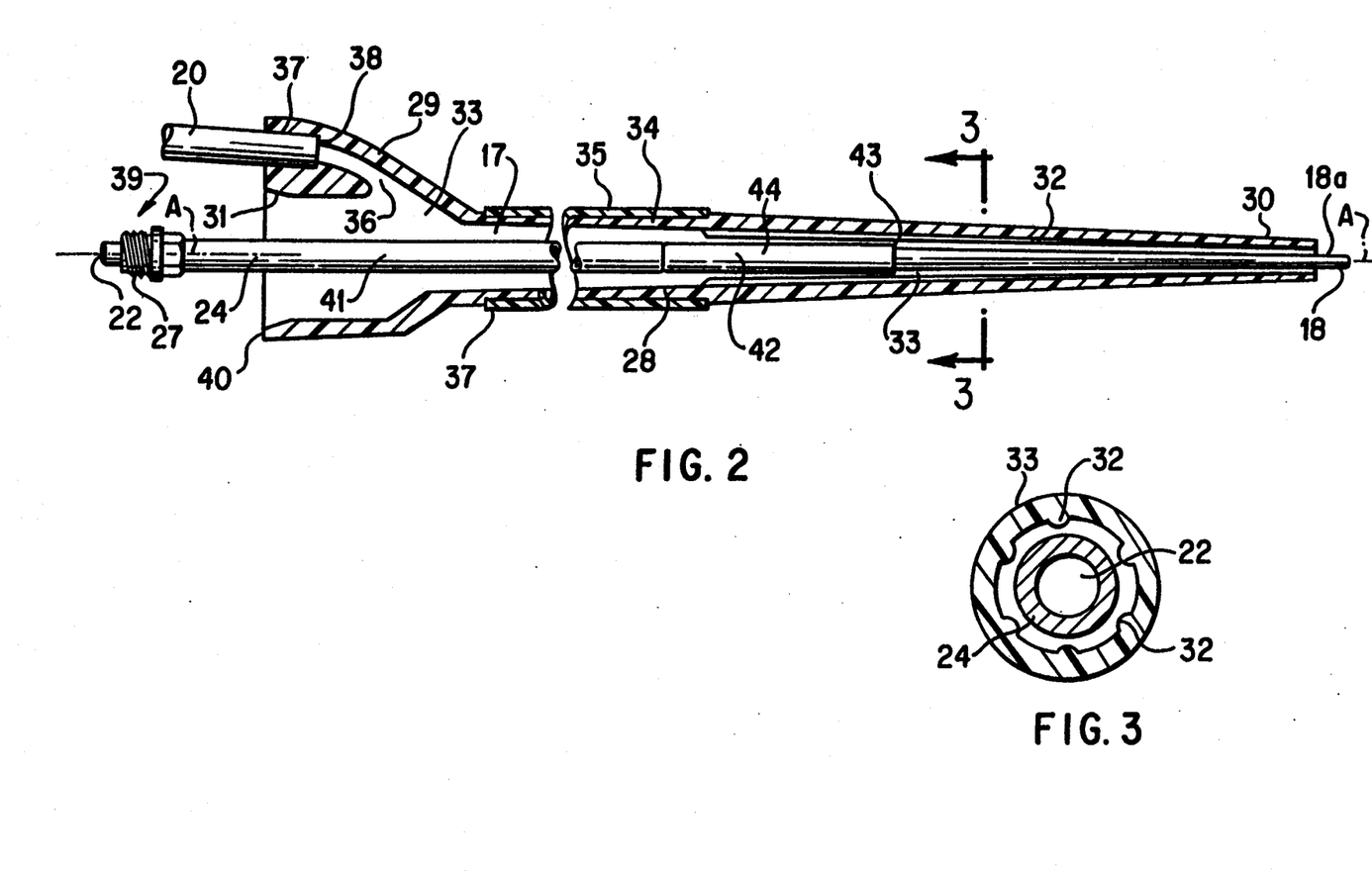
FIG. 2 is a side view of a flue in cross section and an elongate tapered pipe tool therein and has their relative coaxial disposition as would be seen if the cross section were taken along line 2—2 in FIG. 1.
FIG. 3 is a view in cross section of the flue and the elongate tapered pipe tool of FIG. 2 as would be seen if the cross section were taken along line 3—3 in FIG. 2.

In FIG. 2 there is an enlarged side view in cross section of the flue 17 as would be seen along line 2—2 of FIG. 1. In FIGS. 1 and 2, the flue 17 is shown shortened with a section missing as the preferred full length of the flue 17 would not fit on the page without reducing the cross section of the ultrasonic surgical handpiece 10 to an extent such that detail would be lost or to a degree so that the diameter to length relationship would be distorted and any appreciation of the relative lengths of the handpiece 10, flue 17 and cutting tip 18 could not be understood.

In operation the tip 18 is the working end of an elongate tapered hollow metal pipe tool 24, preferably made of titanium alloy tubing of one quarter inch, or 6.3 millimeters, outside diameter and an inside diameter of about 0.078 inch, or 2 millimeters, for high strength, light-weight lower density than the connecting member, and biologically inert. The pipe tool 24, when part of the acoustic vibrator, is designed to vibrate at a preferred frequency of 23,000 cycles per second so that the tip 18 reciprocates longitudinally along axis A with an excursion or peak to peak stroke of about 200 micrometers (0.008 inches) for the preferred embodiment. The irrigation flow through tube 20 passes within an annular space between the flue 17 and the elongate pipe tool 24 picking up heat therefrom.

Figure 4:
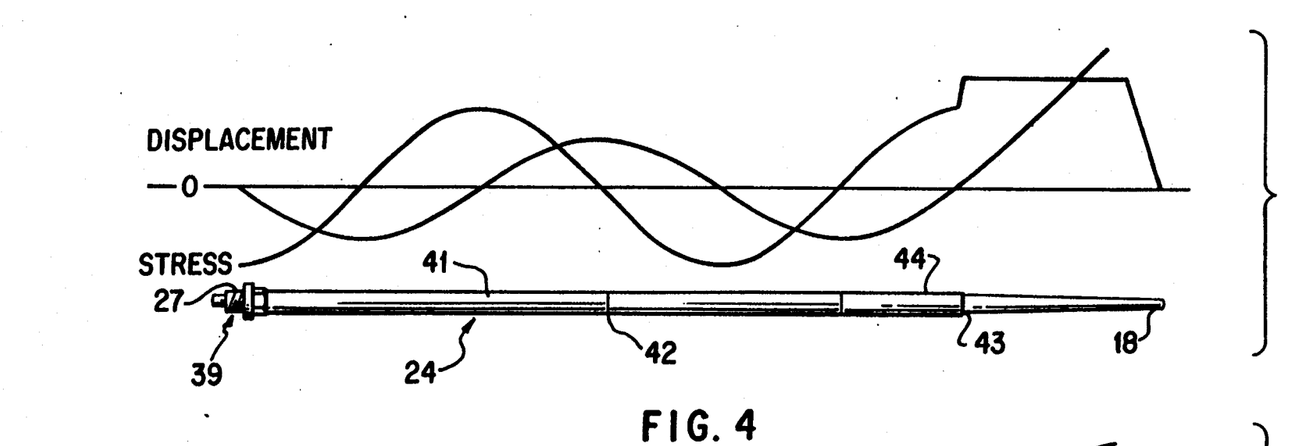
FIG. 4 is an illustration of the pipe tool juxtaposed to plots showing the amplitudes of stress and displacement which occur along its length wherein a pipe tool is elongate to a 7/4 wavelength.
Figure 5:
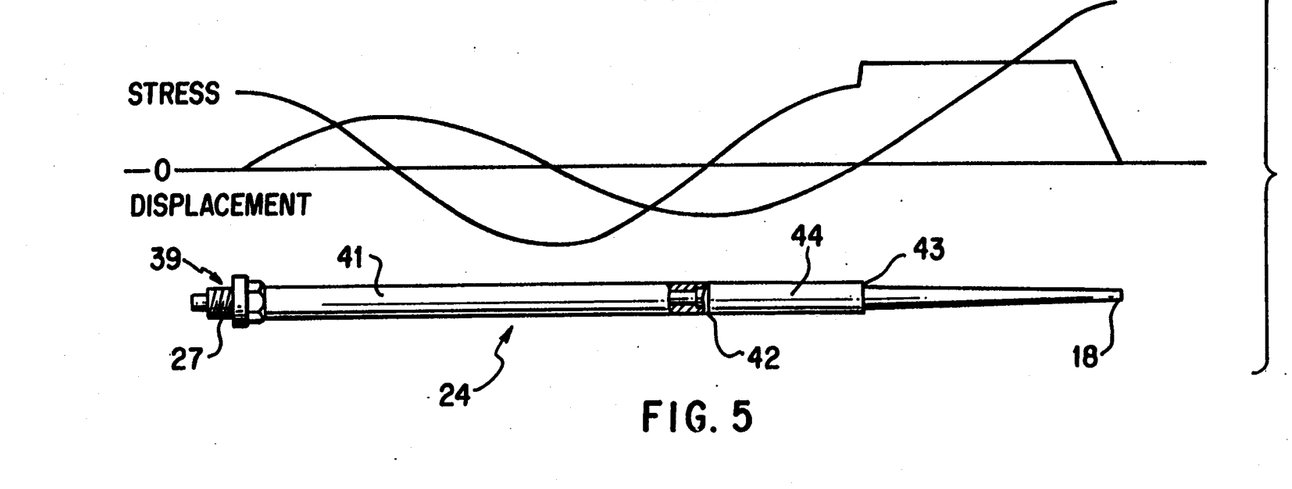
FIG. 5 is an illustration of the pipe tool juxtaposed to plots showing the amplitudes of stress and displacement which occur along its length wherein the pipe tool is elongate to a 5/4 wavelength.

The irrigation fluid is sucked through the preaspiration hole 18a shown in FIGS. 2, 4 and 5 near the tip 18 and returned through connection 23 to tube 21 near the nose cone 15. Thus, irrigant flows and can while cooling aid the movement of debris, such as cut tissue and blood up from the surgical site through bore 22 for removal. Longitudinal ultrasonic vibrations of tip 18 fragment tissue which it contacts. The excursion or amplitude and frequency of the vibrations are electronically maintained and to some extent are adjustable as will be explained herein so that the vibrations are in accord with the gaussian or harmonic design of elongate pipe tool 24 and the requirements of the surgical procedure being practiced. The operational parameters of the design of the pipe tool 24 for a preferred resonant frequency and tip excursion is shown in FIGS. 4 and 5 which illustrate the 7/4 wavelength and the 5/4 wavelength elongated pipe tools, respectively. The ultrasonic motion of the vibrating tip 18 relates to the configuration and length of the pipe tool 24 and as shown in FIGS. 4 and 5 the displacement at the free end of the vibrating tip 18 is at a maximum. To avoid failure, a portion of the vibrating pipe tool 24 is shaped with a Gaussian curved profile which results in an essentially flat stress notwithstanding the increased displacement of the free end. In a pipe tool made of titanium alloy with the stated preferred dimensions, the axial span of each wavelength at the frequency of 23 kilohertz is about 8.7 inches. The overall length of the pipe tool 24 is thus about 12 inches for 5/4 wavelength and 16 inches for 7/4 wavelength.

Numerous shapes, as well as combinations thereof, have been theoretically treated and used as mechanical resonators. There have been attempts by suitable shaping to extend the zone of maximum elastic stress in the axial direction and thereby make greater amplitudes possible, see U.S. Pat. No. 2,984,154. Since the specific technical application constrained four quantities of the resonance element, namely input, node and output cross section and the transmission ratio, the solution of the resulting problem in variation leads to a function that is Gaussian in profile for the tapered part of the vibrating pipe tool 24.

Tubes 25 and 26 provide circulating coolant to the ultrasonic surgical handpiece 10 as shown by arrows in FIG. 1. As explained acoustic vibration of the transducer 12 converts electrical energy to mechanical longitudinal vibrating motion along axis A and through pipe tool 24 to its vibrating tip 18. The preferred transducer 12 is an acoustic vibrator having a laminated nickel alloy structure which is excited by a magnetic field creating oscillating currents passing through the electrical coil winding 13. Coil winding 13 is excited at 23,000 cycles per second (23 kilohertz) alternating current. The resulting longitudinal oscillating motion of the preferred laminated nickel alloy structure is amplified by a preferred tapered titanium alloy pipe tool 24 which extends from the distal end of the nose cone 15 to the distal end of the vibrating tip 18. The pipe tool 24 attaches with threads 27 to the transducer 12 by way of the connecting member 14 interposed therebetween. The taper and wall of the extending titanium pipe tool 24 is designed to be a mechanical structure such that it vibrates at 23,000 cycles per second.

An embodiment of flue 17 shown in FIG. 2, is composed of two composite pieces which may preferably be made of different polymeric materials since the extremities of the flue 17 should preferably be soft and flexible. There is a central body 28 which is hollow, elongate and semi rigid for extending with and coaxial about the axis A passing longitudinally and centrally therethrough. Central body 28 terminates in a funnel 29 which is proximal and a nozzle 30 which is distal. The flue 17 is primarily and preferably made of silicone rubber that has a relatively resilient quality whereby the funnel 29 fits tightly over the nose cone 15 of the ultrasonic surgical handpiece 10 forming a fluid tight gasket like seal 31 due to the rubbery resilient nature of the silicone rubber used.

In FIGS. 1 and 2, the flue 17 is shown less than its preferred length which is about 11½ inches or 29 centimeters. The diameter at the funnel 29 is such that the flue 17 tapers generally toward its nozzle 30. The central body 28 is hollow throughout. Reinforcing ridges 32 extend longitudinally inside the nozzle 30. A recess 34 may circumscribe the exterior of central body 28 and extend proximally from the funnel 30 to the taper of the nozzle 30. The recess 34 is designed to receive a hollow support surrounding cylinder 35 thereabout for reinforcement thereof in the embodiment shown. The hollow support surrounding cylinder 35 is preferably an extruded polysulfone tubular configuration sized to sit within the recess 34 for reinforcement against bending of central body 28. Alternately, the central body 28 can be made of a stiffer construction, i.e. thicker wall or of a coextruded material having a greater modulus since the cross sectional appearance of such a stiffer molded material would not be apparent, that integral construction is not specifically shown in the FIGURES. Skilled artisans would appreciate how that could be accomplished.

Funnel 29 which is generally enlarged diametrically relative to axis A and the rest of the central body 28. The funnel 29 includes a fluid communication port 36 between its inside and outside. The port 36 is arranged to pass fluid from tube 20 which seats within a shouldered opening 37 therein and extends distally from a proximal face 38 thereof. Fluid may pass from the tube 20 through the port 36 into flue 17 and more particularly, the annular space 33 between the flue 17 and the pipe tool 24. The reinforcing ridges 32 support the nozzle 30 (that has a smaller cross sectional area than the funnel 29 or central body 28) maintaining concentricity relative to the tapered titanium vibrating pipe tool 24 near vibrating tip 18 which passes coaxially therethrough, see FIGS. 2 and 3. More importantly, ridges 32 do not clamp the pipe tool 24 or the vibrating tip 18 but still separate the flow of irrigation and coolant so that it passes in laminar fashion along the pipe tool 24 and to the tip 18. Consequently, the coolant is channelled so the flow is between the ridges 32.

In particular and as best seen in FIGS. 2, 4 and 5 the elongate tapered pipe tool 24 has the vibrating tip 18 at its patient contacting extreme (for fragmenting) and a threaded fitting 39 at its proximal extreme (for attachment). Threads 27 allow removable connection of the elongate tapered pipe tool 24 to the connecting member 14 as shown in FIG. 1. The elongate tapered pipe tool 24 is preferably made of an extender 41 having the threads 27 and a straight pipe of about six inches or 15 centimeters length with a diameter of one quarter inch or about seven millimeters. The extender 41 is hollow having an inside diameter of 0.078 inch or 2 millimeters. Threaded connections, shown in partial section in FIG. 5 on the distal end of the extender 41 (away from the threads 27), cooperate with the posterior 42 of the vibrating tip 18 of the tool 24. That is to say that, the tool 24 is composed of the vibrating tip 18 which tapers to a diameter at its anterior of 0.100 inch or 2.5 millimeters. The posterior diameter is seven thirty seconds inches or six millimeters and the length oft he tip 18 is three and one half inches or nine centimeters. A slight shoulder 43 defines the beginning of a hollow cylinder 44 that is two and one eight inches or five and one half centimeters and one quarter inch or about seven millimeters in diameter. The hollow cylinder 44 is held to the extender 41 by the threaded connection so the overall length of the elongate tapered pipe tool 24 is about twelve inches or thirty centimeters for the 5/4 wavelength length pipe tool 24. The 7/4 wavelength is a ½ wave length longer or about 4.3 inches longer or about nine and one half centimeters. The added length is due to a hollow spacer 42 shown in FIG. 4 added between the distal end of extender 41 and the hollow cylinder 44. The hollow spacer 42 is also the same diameter inside and out as the hollow cylinder 44.

Figure 6:
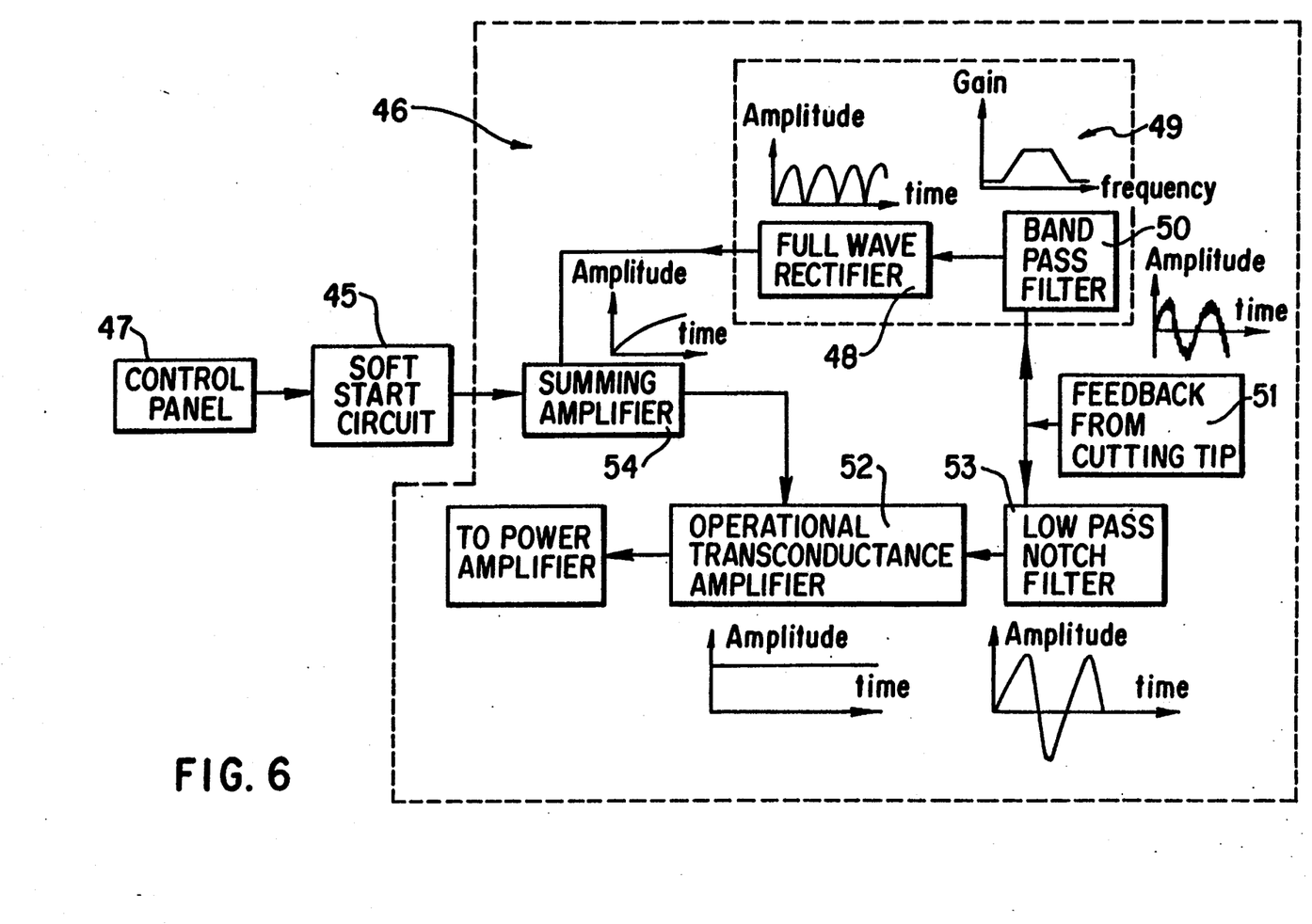
FIG. 6 is a schematic block diagram of the electronic components that drive the ultrasonic surgical handpiece of FIG. 1 at 23 kilohertz.

The ultrasonic surgical handpiece 10 is driven by an energy initiator 45, also referred to herein as the soft start or circuit 45 for a frequency regulator. Circuit 45 is schematically depicted in the block diagram of FIG. 6 and more specifically shown in FIG. 7. The energy initiator 45 for frequency regulation maintains a preset vibrational mode and the linear dynamics of the vibrating tip 18 as driven by the ultrasonic surgical handpiece 10 capable of operation at resonance characteristics and under varying loads. An electronic oscillator 46 drives the ultrasonic surgical handpiece 10 at a predetermined frequency, preferably 23 kilohertz. An amplitude control on the control panel 47 in FIG. 6 is connected to the electronic oscillator 46. The control panel 47 amplitude control permits manual setting of the level of the ultrasonic vibration. A frequency regulator preferably in the form of a full wave rectifier 48 connects between the control panel 47 amplitude control and the electronic oscillator 46. A frequency control feedback loop 49 includes the frequency regulator and is designated by a dashed line forming a block about the full wave rectifier 48 and the band pass filter 50. The frequency control feedback loop 49 maintains the linear dynamics of the ultrasonic surgical handpiece 10 and vibrating pipe tool 24 about the predetermined frequency during use. Feedback 51 from the cutting pipe tool 24 is delivered to the frequency control feedback loop 49 through the band pass filter 50 therein.

An operational transconductance amplifier 52, included as part of the electronic oscillator 46, controls gain for the frequency control feedback loop 49. Specifically, feedback from the cutting tip 51 is delivered to the operational transconductance amplifier 52 through a low pass notch filter 53. Pulse wave diagrams are shown throughout FIG. 6 to illustrate the effect of the circuit components (shown as blocks therein) and to define the operation of a preferred embodiment of the electronic oscillator 46.

The soft start circuit 45 connected to the control panel 47 amplitude control retards the rate of the current application per unit of time to the operational transconductance amplifier 52 to ameliorate the effects of transients on the ultrasonic surgical handpiece 10 vibrating pipe tool 24. The soft start circuit 45 shown in FIG. 7 energizes the circuit 45 in one direction for retarding the rate of current application per unit of time and upon deenergization resets the circuit to ready it for retarding the rate of the current application per unit of time to the operational transconductance amplifier. When the ultrasonic surgical instrument 10 is subject to the effects of transients during restarting or loading, the circuit 45 is ready to retard input to the operational tranconductance. The preferred switching system may be a amplifier transistor which is used to charge and discharge a capacitor in accord with initiation and shut off of the electronic oscillator 46. The effect of this is shown in the pulse wave diagram above, a summing amplifier 54 in FIG. 6.

Figure 7:
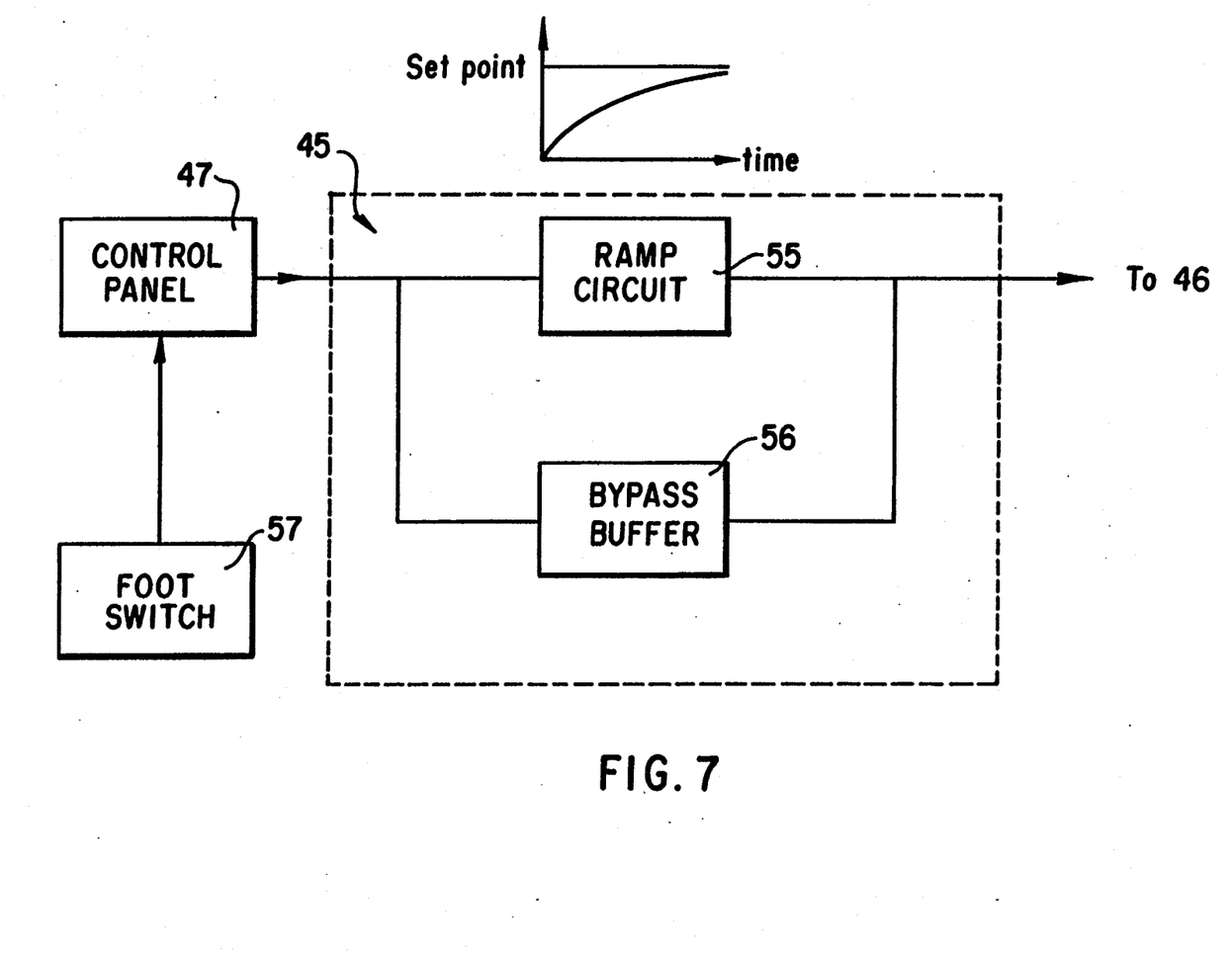
FIG. 7 is a schematic block diagram of the soft start or energy initiator circuit shown as a block in FIG. 6 with the details of a preferred energy initiator having a ramp circuit controlled by the charging rate of a capacitor.

FIG. 7 has the soft start circuit 45 shown as a dashed line block including a ramp circuit 55 in parallel with a bypass buffer 56. Power flow from the control panel 47 as authorized by a foot switch 57 or otherwise sends current to the ramp circuit 55 if the electronic oscillator 46 is not operating and soft start circuit 45 is set to begin. A capacitor in the ramp circuit 55 is charged thus providing a rate dependent start.

The operational transconductance amplifier 52 is a current output device wherein the output current therefrom is directly proportional to its bias current and input voltage so that under steady state operation the bias current acts as the gain or amplitude adjustment for the frequency control feedback loop 49. The soft start circuit 45 connects to the amplitude control for retarding the rate of the bias current application per unit of time to the operational transconductance amplifier 52 thereby limiting the bias current applied to the operational transconductance amplifier 52 during start up and thereby modifies the frequency response and output current therefrom.

The soft start circuit 45 connects to the control panel 47 amplitude control for retarding the rate of the bias current application per unit of time to the operational transconductance amplifier 52. The soft start circuit is similarly capable of limiting the rate of peak bias current application to the operational transconductance amplifier 52 preventing overdriving bias current during start up. The soft start circuit 45 may include a resistance/capacitance network for delaying the application of the fully bias current to the operational transconductance amplifier 52 so already explored.

What is claimed is:

1. An energy initiator for a frequency regulator to maintain a preset vibrational mode and the linear dynamics of an ultrasonic surgical instrument capable of operation at resonance characteristics and under varying loads comprising:
    an electronic oscillator for driving the ultrasonic instrument at a preset vibrational mode;
    an amplitude control connected to the electronic oscillator permitting setting and maintaining of the level of the ultrasonic vibration under varying load;
    a frequency regulator between the amplitude control and the electronic oscillator;
    a frequency regulator between the amplitude control and the electronic oscillator;
    a frequency control feedback loop in the frequency regulator for maintaining the linear dynamics of the ultrasonic surgical instrument about the preset vibrational mode;
    an operational amplifier included as part of the electronic oscillator for gain control for the frequency control feedback loop, and
    a circuit connected to the amplitude control for retarding the rate of the current application per unit of time to the operational amplifier to ameliorate the effects of transients on the ultrasonic surgical instrument.

2. A flue for an ultrasonic surgical handpiece having an elongate pipe tool that vibrates, the flue forming a space surrounding the pipe tool and extending from the handpiece to a vibrating tip on the pipe tool, the flue comprising:
    a central body which is hollow elongate for extending with and about an axis passing centrally therethrough and through the pipe tool;
    a funnel at one end of the central body as a proximal portion thereof to first receive the vibrating tip when inserted therewithin and the pipe tool when inserted therethrough, the funnel shaped to cooperatively engaged with and about the handpiece; and
    a nozzle opposite the funnel on the central body, the nozzle extending from the central body toward and about the vibrating tip of the ultrasonic surgical handpiece;
    a space between the central body and the pipe tool, the space extending axially between the nozzle and the vibrating tip, the space for directing flow of fluid about the pipe tool and the vibrating tip, and
    the flue wherein the central body is made of a material having a durometer higher than that of the nozzle.

3. The flue for an ultrasonic handpiece of claim 2 wherein the modulus of elasticity of the central body is greater than the modulus of elasticity of the nozzle.

4. The flue for an ultrasonic handpiece of claim 3 wherein the nozzle is a silicone polymer material.

5. The flue for an ultrasonic handpiece of claim 2 wherein the nozzle includes internal portions configured to direct fluid flow about the vibrating tip and which internal portions may cooperatively engage the vibrating tip without damping the ultrasonic vibration thereof.

6. The flue for an ultrasonic handpiece of claim 2 wherein the space is generally annular.

7. The flue for an ultrasonic handpiece of claim 2 wherein the nozzle is held to the central body in position relative thereto and substantially concentric with respect to the axis of the pipe tool.

8. An electromechanical oscillating system including a mechanical reverberating system for tuning of the resonance frequency of a mechanical structure designed to vibrate in harmony with the spring constant of the system and a handpiece for carrying replaceable mechanical structures in the form of ultrasonic surgical tools of various different lengths and/or configurations, comprising:
    a housing extends along an axis for the handpiece, the housing being hollow and held proximally during use;
    a transducer within the housing, the transducer positioned along an axis and selected for oscillating along the axis with motion sufficient for surgery and at around at least one preferred frequency and wavelength,
    an electronic oscillator circuit connected to the transducer for initiating and driving the transducer to oscillate at the preferred frequency and wavelength;

a member fitted to the transducer and extending distally from the transducer along the axis within the housing;

ultrasonic surgical tools attachable to the connecting member so that each tool may be of different lengths and/or configurations tuned to oscillate around at least the preferred frequency and wavelength;

a flue extending from the handpiece housing distally about the ultrasonic surgical tool that vibrates;

a body on the flue, the body which is hollow and elongate for extending with and about the axis passing centrally therethrough and through the pipe tool;

a funnel at an end of the body as a proximal portion thereof to first receive the vibrating tip when inserted therewithin and the ultrasonic surgical tool when inserted therethrough, the funnel shaped to cooperatively engaged with and about the housing; and a nozzle opposite the funnel on the central body, the nozzle extending from the body toward and about the vibrating tip of the ultrasonic surgical tool;

a space between the body and the ultrasonic surgical tool, the space extending axially between the nozzle and the vibrating tip, the space for directing flow of fluid about the ultrasonic surgical tool and the vibrating tip, and the flue wherein the body is made of a material having a durometer higher than that of the nozzle.

9. The system of claim 8 wherein the modulus of elasticity of the body is greater than the modulus of elasticity of the nozzle.

10. The system of claim 9 wherein the nozzle is a silicone polymer material.

11. The system of claim 8 wherein the nozzle includes internal portions configured to direct fluid flow about the vibrating tip and which internal portions may cooperatively engage the vibrating tip without damping the ultrasonic vibration thereof.

12. The system claim 8 wherein the space is generally annular.

13. The system of claim 8 wherein the nozzle is held to the body in position relative thereto and substantially concentric with respect to the axis of the ultrasonic surgical tool.

* * * * *